US011096650B2

(12) United States Patent
Judkins et al.

(10) Patent No.: US 11,096,650 B2
(45) Date of Patent: Aug. 24, 2021

(54) DIRECT ACCELERATION MEASUREMENT OF A SUBJECT SUPPORT

(71) Applicant: KONINKLIJKE PHILIPS N.V., Eindhoven (NL)

(72) Inventors: Daniel David Judkins, Richmond Heights, OH (US); Marc Anthony Chappo, Elyria, OH (US)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 522 days.

(21) Appl. No.: 15/746,814

(22) PCT Filed: Aug. 1, 2016

(86) PCT No.: PCT/IB2016/054606
§ 371 (c)(1),
(2) Date: Jan. 23, 2018

(87) PCT Pub. No.: WO2017/025852
PCT Pub. Date: Feb. 16, 2017

(65) Prior Publication Data
US 2020/0077970 A1    Mar. 12, 2020

Related U.S. Application Data

(60) Provisional application No. 62/204,081, filed on Aug. 12, 2015.

(51) Int. Cl.
*A61B 6/00* (2006.01)
*A61B 6/04* (2006.01)
(Continued)

(52) U.S. Cl.
CPC ............ *A61B 6/547* (2013.01); *A61B 6/0407* (2013.01); *A61B 6/0487* (2020.08); *A61B 6/107* (2013.01);
(Continued)

(58) Field of Classification Search
CPC .............................. A61B 6/5276; A61B 6/586
See application file for complete search history.

(56) References Cited

U.S. PATENT DOCUMENTS 6,461,040 B1 * 10/2002 Mattson .................. A61B 6/08
378/205
8,457,279 B2    6/2013 Saracen
(Continued)

FOREIGN PATENT DOCUMENTS

CA        2721794 A1    5/2012
WO      2014013302        1/2014

*Primary Examiner* — Yi-Shan Yang
(74) *Attorney, Agent, or Firm* — Larry Liberchuk

(57) ABSTRACT

A subject support includes a fixed portion and a moveable portion coupled to the fixed portion and configured to move along at least one axis relative to the fixed portion, and the coupling includes one or more points of friction that move during movement of the moveable portion and which wear due to at least movement by the moveable portion. The moveable portion receives and supports at least one of an object or a subject during an imaging procedure with an imaging device. One or more inertial measurement units (IMUs) are affixed to or embedded in the moveable portion that directly measure acceleration of translation of the moveable portion along one or more axes.

18 Claims, 2 Drawing Sheets

(51) Int. Cl.
*A61B 6/10* (2006.01)
*A61B 6/03* (2006.01)
*A61B 5/055* (2006.01)

(52) U.S. Cl.
CPC ............ *A61B 6/5276* (2013.01); *A61B 6/586* (2013.01); *A61B 5/055* (2013.01); *A61B 6/032* (2013.01); *A61B 6/037* (2013.01)

(56) References Cited

U.S. PATENT DOCUMENTS

| | | |
|---|---|---|
| 9,132,549 B2 | 9/2015 | Kaiser |
| 2005/0234327 A1* | 10/2005 | Saracen ................. A61B 6/548 600/407 |
| 2011/0158387 A1 | 6/2011 | Narayanaswamy |
| 2013/0025055 A1 | 1/2013 | Saracen |
| 2015/0272481 A1* | 10/2015 | Glaser ................. G06F 19/3418 600/301 |
| 2015/0306340 A1* | 10/2015 | Giap ...................... G16H 20/40 600/301 |
| 2016/0029952 A1* | 2/2016 | Hunter ...................... A61F 2/32 623/22.17 |
| 2017/0205519 A1* | 7/2017 | Robert ................... G01V 1/201 |

* cited by examiner

DIRECT ACCELERATION MEASUREMENT OF A SUBJECT SUPPORT

CROSS REFERENCE TO RELATED APPLICATIONS

This application is the U.S. National Phase application under 35 U.S.C. § 371 of International Application No. PCT/I132016/054606, filed Aug. 1, 2016, published as WO 2017/025852 on Feb. 16, 2017, which claims the benefit of U.S. Provisional Patent Application No. 62/204,081 filed Aug. 12, 2015. These applications are hereby incorporated by reference herein.

FIELD OF THE INVENTION

The following generally relates to measurement of acceleration of a medical imaging subject support during an imaging procedure.

BACKGROUND OF THE INVENTION

During an imaging procedure, such as a Computed Tomography (CT), Magnetic Resonance (MR), Positron Emission Tomography (PET), and the like, a patient or subject rests on a subject support, such as a couch or tabletop. The subject support is advanced into an imaging region of an imaging device where signals indicative of characteristics of the subject are measured, such as attenuated x-rays, electromagnetic field changes, emitted gamma photons, and the like. The advancement along an axis through the imaging region is a z-axis. The advancement can include lifting or elevating the subject support to pass through the imaging region and/or bore of the imaging device, which is along a y-axis.

Detection and/or reconstruction algorithms for measuring the characteristics of the subject depend on knowing the precise position of the subject in the imaging region at a designated time. The subject support is manufactured of materials substantially transparent to the signals, and other objects or devices are minimized or eliminated in the imaging region, which may interfere with the signals. Motors and drive mechanisms with rates of acceleration and velocity within tolerances calculated based on expectations are used to move the subject support in a region of safety known as a collision avoidance envelope. In some approaches, the velocity and/or acceleration are computed from changes in position using position markers and clock time, e.g. expected velocity and/or acceleration as first and second order derivatives of changes in position.

Points of friction which move the subject support, such as screws, gears, or bearings, wear over time. As the points of friction wear, the worn points of friction can change the acceleration and/or velocity of the subject support during the imaging procedure. For example, the subject support may not accelerate/decelerate to a desired position at a designated time, e.g. ramp up/down, or may not travel at a constant velocity. As such, detecting when the points of friction are sufficiently worn or about to be worn can be helpful to schedule field maintenance. Furthermore, knowing which points of friction are sufficient worn or about to be worn beyond acceptable tolerances can provide information about individual parts to be replaced and tracking supply, e.g. defective batch, targeted replacement, preventative maintenance, and the like.

Another issue with the proper positioning of subject support is deflection. As the subject support is advanced into the imaging region, the subject support is supported at one end or one side of the imaging region and/or imaging device bore. The unsupported end of the subject support is deflected, e.g. sags. Supporting the subject support inside the bore or imaging region typically places components/materials which can interfere with the signals in the imaging region and/or bore. Variable patient sizes and loads cause different deflections which can affect imaging procedures. One approach to address deflection is to include a support on the other side of the imaging region and/or imaging device bore, such as a roller, which catches and minimizes the deflection of the subject support. Another approach is the use of lasers positioned just outside the imaging region and/or imaging device bore avoiding interference with the signals, and the lasers with mirrors and/or light sensors identify a deflected position of the subject support. Yet another approach is to simulate loads according to patient age, height and weight, and to use look-up tables during imaging procedures to determine an expected deflection according to age, height and weight of the patient undergoing an imaging procedure.

SUMMARY OF THE INVENTION

Aspects described herein address the above-referenced problems and others.

The following describes direct acceleration measurement of a subject support. The direct acceleration measurement is through at least one inertial measure device (IMU) affixed to or embedded in the subject support, which measures acceleration at least along one axis of movement. In another embodiment, one or more shielded IMUs affixed to or embedded in the subject support measures acceleration along two axes of movement.

In one aspect, a subject support includes a fixed portion and a moveable portion coupled to the fixed portion and configured to move along at least one axis relative to the fixed portion, and the coupling includes one or more points of friction that move during movement of the moveable portion and which wear due to at least movement by the moveable portion. The moveable portion receives and supports at least one of an object or a subject during an imaging procedure with an imaging device. One or more inertial measurement units (IMUs) are affixed to or embedded in the moveable portion that directly measure acceleration of translation of the moveable portion along one or more axes.

In another aspect, a method of measuring movement of a subject support includes directly measuring acceleration of a moveable portion coupled to a fixed portion with points of friction between the moveable portion and the fixed portion, and the moveable portion moving along at least one axis relative to the fixed portion, and one or more inertial measurement units (IMUs) affixed to or embedded in the moveable portion directly measure acceleration of the moveable portion translating along one or more axes.

In another aspect, a method of measuring movement of a subject support includes directly measuring acceleration of a moveable portion with points of friction between the moveable portion and a fixed portion, and the moveable portion moving along at least one axis relative to the fixed portion, and one or more inertial measurement units (IMUs) affixed to or embedded in the moveable portion directly measure acceleration of the moveable portion translating along one or more axes. The directly measured acceleration along the at least one axis is indicative of wear by the points of friction is evaluated and a signal for maintenance is generated.

BRIEF DESCRIPTION OF THE DRAWINGS

The invention may take form in various components and arrangements of components, and in various steps and arrangements of steps. The drawings are only for purposes of illustrating the preferred embodiments and are not to be construed as limiting the invention.

DETAILED DESCRIPTION OF EMBODIMENTS

Figure 1:
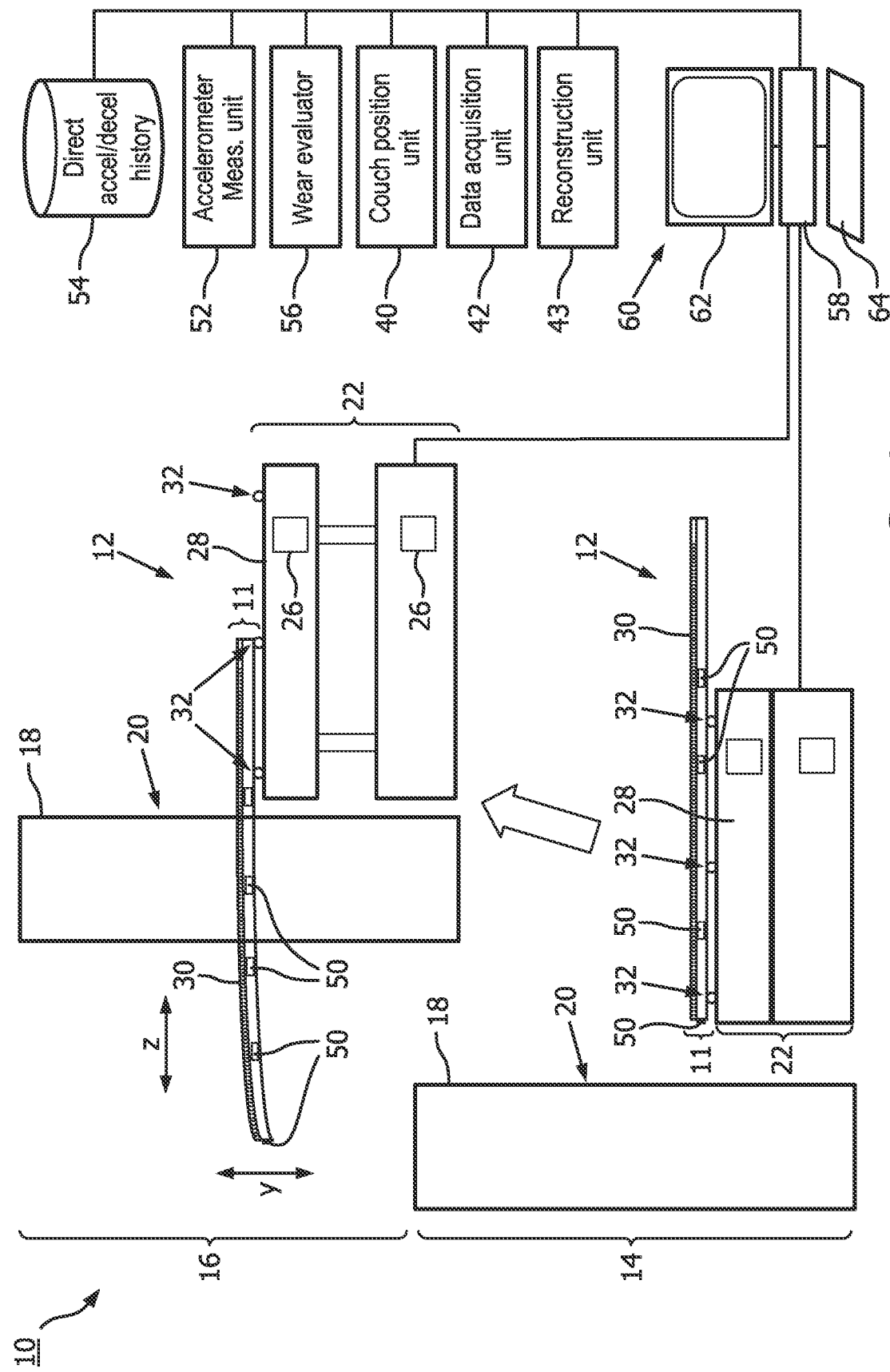
FIG. 1 schematically illustrates an embodiment of an imaging system with direct acceleration measurement of a moveable portion of a subject support.

Initially referring to FIG. 1, an example imaging system 10 with a direct acceleration measurement of a moveable portion 11 of a subject support 12 is schematically illustrated in a patient loading position 14 and a fully extended position 16 with deflection of the moveable portion 11 of the subject support 12 exaggerated. The imaging system includes one or more imaging devices 18 or modalities, such as CT, MR, PET and the like, which are shown in a partial cross section. The imaging device 18 includes an imaging region and/or bore 20. During an imaging procedure, the moveable portion 11 is moved through the imaging region 20, e.g. translated along a z-axis.

The subject support 12 includes a base 22 and a tabletop or the moveable portion 11. The base 22 includes one or more motors 26 and electrical connections. The base 22 supports the moveable portion 11 and provides for movement of the moveable portion 11 relative to the base 22 and to the imaging device 18, e.g. moves as a single structure translated along one or two axes. In some embodiments, as illustrated, the subject support 12 can include an intermediate portion 28 which provides for vertical movement (y-axis) of the moveable portion 11, e.g. lifting or elevating the moveable portion 11. In some embodiments, the intermediate portion 28 is included in the base 22 or the moveable portion 11 and provides both vertical (y-axis) and horizontal (z-axis) movement. As the moveable portion 11 moves beyond or is extended beyond the base 22, the moveable portion 11 extending beyond deflects, e.g. sags. The amount of deflection can vary with the load and distribution of the subject/object and can vary along the length (parallel to z-axis) of the moveable portion 11.

The subject support 12 can include position indicators 30, such as visible marking on the moveable portion 11 and/or the base 22. The position indicators 30 are known the imaging system 10 through position sensors. The subject support includes points of friction 32, such as a lead screw and nut, screws, bearings, gears, and the like. The points of friction 32 include couplings between the moveable portion 11, the base 22 and/or the intermediate portion 28. The points of friction 32 can include other points of friction, such components between the motors 26 and the moveable portion 11, which wear during movement of the moveable portion 11.

The imaging system 10 includes a couch position unit 40 which identifies the position of the moveable portion 11 relative to the imaging region 20.

A data acquisition unit 42 acquires signals indicative of characteristics of a portion of the subject located in the imaging region 20. The acquired signals can be acquired during movement of the moveable portion 11, e.g. at a predetermined velocity, in between acceleration/deceleration, and the like. The acquired signals can be acquired at predetermined start and end positions identified by the couch position unit 40. The data acquisition unit 42 can include acquisition parameters based on the position of the moveable portion 11 and/or subject location relative to the moveable portion 11 and imaging region 20.

A reconstruction unit 43 reconstructs the acquired signal into one or more images according to a reconstruction algorithm and reconstruction parameters which can include subject position. The reconstruction algorithm and parameters include techniques known in the art.

The moveable portion 11 includes one or more inertial measurement units (IMUs) 50 affixed to or embedded in the moveable portion 11. The IMUs 50 are configured to measure acceleration/deceleration along two axis, which include vertical movement and/or deflection (y-axis), and horizontal direction (z-axis). The IMUs 50 are located to minimize visibility to acquired imaging signals. In one embodiment, an IMU 50 is affixed to and/or embedded in a leading end and/or first frame of the moveable portion 11. In another embodiment, IMUs 50 are distributed along a length of the moveable portion 11, e.g. along one or both sides, correspond to image or acquisition frames, correspond to distances between points of friction, and the like. For example, a two axis accelerometer mounted to a leading edge of the tabletop measures elevation while raising the tabletop and subject/object level with the examination region on a y-axis, measures acceleration during ramp up/ramp down, changes to an expected constant velocity during scanning while the tabletop moves on a z-axis, and measures deflection of the leading edge on a y-axis as the leading edge is cantilevered through the examination region. In another example, accelerometers spaced along a lateral edge measure acceleration during ramp up/down along a z-axis, changes to an expected constant velocity as non-zero acceleration (+/−) during scanning along the z-axis, and deflection at each position of each accelerometer during scanning along the y-axis as the tabletop moves through the examination region and is cantilevered.

The IMUs 50 include solid state components and can be acquired commercially, which can be shielded from scattered or direct radiation and/or electromagnetic fields, such as with a Lead (Pb), Aluminum (Al) cover or other high z material, a conductive mesh material for a Faraday cage, and/or use radiation hardened Silicon (Si). In some embodiments, the moveable portion 11 includes carbon fiber which can be used as a high impedance ground to minimize wires from the IMUs 50. The IMUs 50 can include printed or painted wiring on a surface of the moveable portion 11. The IMU 50 components, material, and/or placement are selected to minimize image artifacts and/or signal interference. For example, the IMUs are placed along an outer edge or outside edge of the moveable portion, oriented to minimize z-axis area, avoid overlap with normal patient positioning, and the like. The IMUs 50 are communicatively connected to an acceleration measurement unit 52. In some embodiments, the IMUs are powered and communicatively connected through the base portion 22. In some embodiments, the IMUs received power through currents induced by electromagnetic fields, such as with MR. In some embodiments, the IMUs receive power through battery. In some embodiments, the IMUs communicate wirelessly. In some instances, the IMUs 50 minimize image artifacts and/or signal interference.

The accelerometer measurement unit 52 receives the direct acceleration measurements from each of the IMUs 50, and stores the measurements in a direct acceleration/deceleration data store 54. The direct acceleration/deceleration data store 54 can include transitory or non-transitory computer memory, such as solid state storage, disk storage, cloud storage, server storage, and the like. The measurements include the directly measured acceleration/deceleration rate (distance/time$^2$) by each IMU 50 for each axis measured, e.g. y-axis, z-axis, and an identifier of the IMU 50. The measurements can include a time, a couch position, an image frame, motor control commands, an imaging protocol or other associated data which relates to associating the direct acceleration measurement with the points of friction 32.

In one embodiment, the accelerometer measurement unit 52 communicates the y-axis measurement to the couch position unit 40, which identifies adjustment to the y-axis position of the moveable portion 11 and supported portion of patient within the imaging region 20, according to the acquired imaging data and subsequently to the reconstructed image. For example, each IMU can provide a directly measured acceleration from which a deflection can be computed for the position on the moveable portion 11 where the corresponding IMU is located. In some instances, the adjustments due to spaced IMUs 50 account for deflection of portions of the moveable portion 11 independent of patient load or size, e.g. weight and/or weight distribution.

A wear evaluator 56 receives the measurements from the direct acceleration/deceleration data store 54 and evaluates the measurements to determine wear on the points of friction 32. In one embodiment, the wear evaluator 56 evaluates the measurements dynamically as the measurements are stored. In another embodiment, the wear evaluator 56 evaluates the measurements at predetermined intervals, such as daily, weekly, after each procedure, and the like. The wear evaluator 56 determines if one or more points of friction 32 exceed predetermined thresholds, e.g. acceptable tolerances. The wear evaluator 56 can use one or more threshold limits to determine if the acceptable tolerances are exceeded. For example, if an acceleration rate/deceleration rate is exceeded for a period of ramping up/down of the tabletop, then a signal can be generated indicating maintenance is indicated or that a region of travel should be avoided. The signal, such as a displayed message, an electronic message communicated over a cellular and/or a computer network, and the like, can include a tabletop position at the time of the ramping up/down. The signal can include wear indications for each of the points of friction based on the direct measurements of the IMUs 50. In some instances, the wear evaluator identifies the points of friction, which are sufficiently worn or about to be worn to allow preventative maintenance.

The couch position unit 40, the data acquisition unit 42, the accelerometer measurement unit 52, and the wear evaluator 56 comprise at least one processor 58 (e.g., a microprocessor, a central processing unit, digital processor, and the like) configured to executes at least one computer readable instruction stored in computer readable storage medium, which excludes transitory medium and includes physical memory and/or other non-transitory medium. The processor 58 may also execute one or more computer readable instructions carried by a carrier wave, a signal or other transitory medium. The processor 58 can include local memory and/or distributed memory. The processor 58 can include hardware/software for wired and/or wireless communications. The processor 58 can comprise a computing device 60, such as a desktop computer, a server, a laptop, a mobile device, combinations and the like. In some embodiments, multiple processors (58) can comprise multiple computing devices (60) to share the workload. The computing device 60 can include a display device 62 and/or one or more input devices 64, such as a keyboard, touch screen, microphone, mouse and the like.

Figure 2:
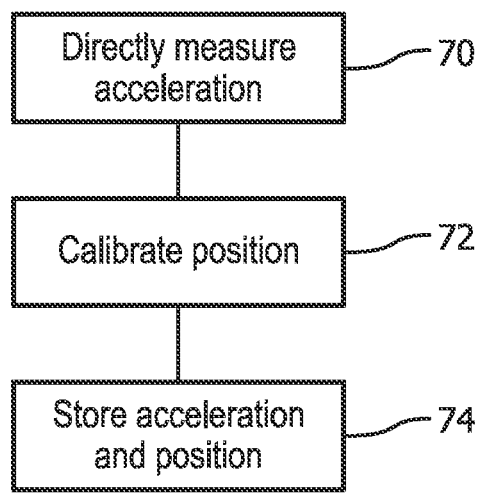
FIG. 2 flowcharts an embodiment of directly measuring subject support movement.

With reference to FIG. 2, an embodiment of directly measuring subject support movement is flowcharted. At 70, direct measurements of acceleration are made and received from one or more IMUs 50 for one or more axes. For example, direct measurements of acceleration are received from one IMU 50 for a z-axis movement of the moveable portion 11 during an imaging procedure. In another example, direct measurements of acceleration are received from one IMU 50 for a y-axis and a z-axis movement of the moveable portion 11 during an imaging procedure. In another example, direct measurements are received from at least one IMU 50 for a z-axis movement, and from IMUs 50 spaced along the z-axis of the moveable portion 11 for y-axis movement during an imaging procedure. The measurements are received by electronic communication between the IMUs and the accelerometer measurement unit 52. The direct measurement includes the acceleration/deceleration rate in known units. The direct measurement can include an identity of the IMU associated with the measurement. The direct measurement can include a time value, e.g. a timestamp, indicative of point in time of the measurement. The direct measurement can include a collection of measurements, e.g. burst transfer.

The direct measurements can occur after a subject or object is loaded onto the moveable portion 11. The direct measurements can occur after a scanning protocol is selected and movement of the moveable portion 11 is determined by the couch position unit 40. The direct measurements can include selected or discrete periods of direct measurement, such as during ramp up or during an expected interval of constant velocity. The direct measurements can include a single axis measurement of direct acceleration, such as a z-axis measurement. The direct measurement can include two axes of measurement which include a z-axis measurement of translation along an axis through an imaging region, a translation of elevating the moveable portion in preparation of moving the moveable portion 11 through the imaging region, and a deflection of segments of the moveable portion 11 moving through the imaging region independently measured by the IMUs at the position of the corresponding IMU. The direct measurements can include two axis measurement, such as a z-axis measurement and a y-axis measurement of one IMU on a leading edge.

At 72, the direct measurements can be used to calibrate one or more positions of the moveable portion 11 according to the position of the moveable portion 11, such as determined by the couch position unit 40, the expected operating characteristics of the motors, and the like. For example, a time and a distance between two position measurements from the couch position unit 40 are used to calculate an acceleration rate during a ramp up which are compared with the direct acceleration measurements. In another example, during a period of expected constant velocity between two positions, a non-zero or an acceleration/deceleration above a threshold indicates a change in velocity. In another example, direct measurements of acceleration in a y-axis direction are used to calculate a distance of deflection. In another, example, direction measurements of acceleration in a y-axis by spaced IMUs are used to calculate distances of deflection of portions of the moveable portion, such as image frames, independent of the patient load and distribution. The results of the calibrations, such as deflection distances, can be used by the data acquisition unit 42 and/or reconstruction unit 43 to adjust data acquisition and/or reconstruction parameters. The calibration can include an evaluation of the calibration by the wear evaluator 56.

At 74, the received direct acceleration measurements are stored in the direct acceleration/deceleration data store 54. The stored direct acceleration measurements can include the received measurements or a portion of the received measurements, such as those exceeding a threshold amount or threshold amount according to anticipated or calculated measurement. The stored measurements can include additional information from the couch position unit 40 and/or the data acquisition unit 42, such as image frame, position of the moveable portion, motor controller commands, anticipated acceleration/deceleration rates, and the like.

Figure 3:
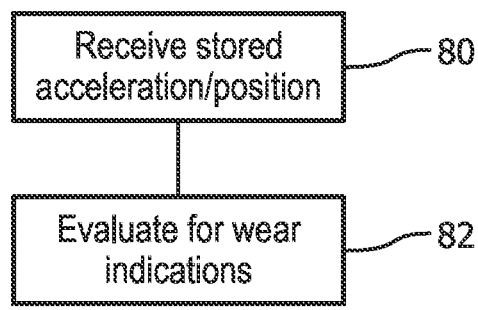
FIG. 3 flowcharts an embodiment of evaluating wear of points of friction using direct measurement of the moveable portion acceleration of a subject support.

With reference to FIG. 3, an embodiment of evaluating wear of points of friction using direct measurement of subject support acceleration is flowcharted.

At 80, the stored direct acceleration measurements are received by the wear evaluation unit 56. Additional information can be received, such as acceleration/deceleration profiles of motors, velocity and acceleration profiles according to imaging procedures, and the like.

At 82, the received direct acceleration measurements are evaluated for wear indications or potential wear evaluations. The wear evaluation can include evaluation differences between direct acceleration measurements and calculated or anticipated measurements according to one or more points of friction. For example, for a difference exceeding a threshold between the direct measurement and calculated acceleration, or between distance as function of the direct measurement and determined position, a wear indication is indicated. The wear indicator can localize the point of friction according to the position or point in time according to the imaging procedure. In another example, differences between the direction measurement and calculated acceleration, or a distance as function of the direct measurement and determined position over a number of imaging operations can be used to predict, e.g. linear regression, or indicate a probable wear indicator within a predetermined period of time. The prediction can be used to initiate a field service to the subject support 12. In some instances, the evaluation can include identified points of friction contributing to the wear indications.

The above may be implemented by way of computer readable instructions, encoded or embedded on computer readable storage medium, which, when executed by a computer processor(s), cause the processor(s) to carry out the described acts. Additionally or alternatively, at least one of the computer readable instructions is carried by a signal, carrier wave or other transitory medium.

The invention has been described with reference to the preferred embodiments. Modifications and alterations may occur to others upon reading and understanding the preceding detailed description. It is intended that the invention be construed as including all such modifications and alterations insofar as they come within the scope of the appended claims or the equivalents thereof.

The invention claimed is:

1. A subject support, comprising:
   a moveable portion coupled to a fixed portion and configured to move along at least one axis relative to the fixed portion;
   one or more points of friction configured to move during movement of the moveable portion,
      wherein the one or more points of friction wear out due to at least movement by the moveable portion, and
      wherein the moveable portion is configured to receive and support at least one of an object and a subject during an imaging procedure with an imaging device;
   one or more inertial measurement units (IMUs) affixed to or embedded in the moveable portion, wherein the one or more IMUs directly measure acceleration of translation of the moveable portion along one or more axes;
   an accelerometer configured to receive the directly measured acceleration from each of the one or more IMUs and store measurements that comprises the directly measured acceleration; and
   at least one processor configured to receive the measurements and evaluate the directly measured acceleration for wear indications to the one or more points of friction.

2. The subject support according to claim 1, wherein the one or more IMUs include a shield from radiation emitted by the imaging device.

3. The subject support according to claim 1, wherein at least one of the one or more IMUs is located on at least one of a leading edge or a lateral edge of the moveable portion.

4. The subject support according to claim 1, wherein the moveable portion is configured to move along a z-axis through an imaging region of the imaging device, and the one or more IMUs are configured to directly measure acceleration along the z-axis.

5. The subject support according to claim 1, wherein the movement along a y-axis includes at least one of elevation or deflection, and the one or more IMUs directly measure acceleration along the y-axis.

6. The subject support according to claim 1, wherein the one or more IMUs includes a plurality of IMUs spaced along a z-axis of the moveable portion, and wherein the plurality of IMUs independently from each other measure a y-axis acceleration of a corresponding position of the moveable portion.

7. The subject support according to claim 1, wherein the at least one processor is further configured to identify an adjustment to at least one of data acquisition parameters or image reconstruction parameters for the imaging device based on the directly measured acceleration at a position of one of the one or more IMUs along the y-axis of the moveable portion with the subject within an imaging region.

8. The subject support according to claim 1, wherein the measurements further comprise at least one of: a time of the directly measured acceleration, a couch position, an image frame, one or more motor control commands, and an imaging procedure; and
   wherein the at least one processor is further configured to evaluate the measurements for the wear indications based on a difference between an expected acceleration, measured based on changes in position indicators, and a corresponding directly measured acceleration.

9. The subject support according to claim 8,
   wherein the wear indications include a prediction of the measurements exceeding a threshold based on a statistical evaluation of the difference between the expected acceleration and the corresponding directly measured acceleration.

10. A method, comprising:
providing a subject support that comprises a moveable portion coupled to a fixed portion, the moveable portion being configured to move along at least one axis relative to the fixed portion;
providing one or more points of friction on the subject support,
  wherein the one or more points of friction move during movement of the moveable portion and wear out due to at least movement by the moveable portion, and
  wherein the moveable portion is configured to receive and support at least one of an object and a subject during an imaging procedure with an imaging device;
directly measuring acceleration of translation of the moveable portion along one or more axes by one or more inertial measurement units (IMUs) affixed to or embedded in the moveable portion;
receiving, via an accelerometer, the directly measured acceleration from each of the one or more IMUs;
storing, via the accelerometer, measurements that comprise the directly measured acceleration; and
evaluating, by at least one processor, the directly measured acceleration for wear indications to the one or more points of friction.

11. The method according to claim 10, wherein the one or more IMUs include a shield from radiation emitted by the imaging device.

12. The method according to claim 10, wherein at least one of the one or more IMUs is located on at least one of a leading edge or a lateral edge of the moveable portion.

13. The method according to claim 10, wherein the moveable portion is configured to move along a z-axis through an imaging region of the imaging device, and the one or more IMUs are configured to directly measure acceleration along the z-axis.

14. The method according to claim 10, wherein the movement along a y-axis includes at least one of elevation or deflection, and the one or more IMUs directly measure acceleration along the y-axis.

15. The method according to claim 10,
wherein the one or more IMUs includes a plurality of IMUs spaced along a z-axis of the moveable portion, and
wherein the plurality of IMUs independently from each other measure a y-axis acceleration of a corresponding position of the moveable portion.

16. The method according to claim 10, wherein the at least one processor is further configured to identify an adjustment to at least one of data acquisition parameters or image reconstruction parameters for the imaging device based on the directly measured acceleration at a position of one of the one or more IMUs along the y-axis of the moveable portion with the subject within an imaging region.

17. The method according to claim 10,
wherein the measurements further comprise at least one of: a time of the directly measured acceleration, a couch position, an image frame, one or more motor control commands, and an imaging procedure; and
wherein the at least one processor is further configured to evaluate the measurements for the wear indications based on a difference between an expected acceleration, measured based on changes in position indicators, and a corresponding directly measured acceleration.

18. The method according to claim 17,
wherein the wear indications include a prediction of the measurements exceeding a threshold based on a statistical evaluation of the difference between the expected acceleration and the corresponding directly measured acceleration.

* * * * *